(12) United States Patent
Lee (10) Patent No.: US 10,775,367 B2
(45) Date of Patent: Sep. 15, 2020

(54) APTASENSOR AND METHOD OF DETECTING TARGET MATERIAL

(71) Applicant: Ji Hoon Lee, Gaithersburg, MD (US)

(72) Inventor: Ji Hoon Lee, Gaithersburg, MD (US)

(73) Assignee: JI Hoon LEE, Gaithersburg, MD (US)

( * ) Notice: Subject to any disclaimer, the term of this patent is extended or adjusted under 35 U.S.C. 154(b) by 0 days.

(21) Appl. No.: 15/566,557

(22) PCT Filed: Apr. 15, 2016

(86) PCT No.: PCT/US2016/027836
§ 371 (c)(1),
(2) Date: Oct. 13, 2017

(87) PCT Pub. No.: WO2016/168656
PCT Pub. Date: Oct. 20, 2016

(65) Prior Publication Data
US 2018/0275120 A1    Sep. 27, 2018

Related U.S. Application Data

(60) Provisional application No. 62/148,028, filed on Apr. 15, 2015.

(51) Int. Cl.
*A61K 48/00* (2006.01)
*C07H 21/02* (2006.01)
*G01N 33/53* (2006.01)
*C12N 15/115* (2010.01)

(52) U.S. Cl.
CPC ....... *G01N 33/5308* (2013.01); *C12N 15/115* (2013.01); *C12N 2310/16* (2013.01); *C12N 2310/3519* (2013.01); *C12N 2320/10* (2013.01); *G01N 2458/30* (2013.01)

(58) Field of Classification Search
CPC .......................... C12N 15/111; C12N 2310/11
See application file for complete search history.

(56) References Cited

PUBLICATIONS

Mun et al. (Biosensors and Bioelectronics, 58, 2014, 308-313).*
Chong et al. (Biosensors and Bioelectronics, 32, 2012, 19-23).*

* cited by examiner

*Primary Examiner* — Amy H Bowman
(74) *Attorney, Agent, or Firm* — Dentons US LLP (57) ABSTRACT

A method detects a target material in a sample, and includes: providing an aptasensor having a first aptamer capable of binding with hemin; a second aptamer capable of binding with the target material; and a nucleotide linker connecting the first aptamer and the second aptamer, adding hemin to the sample, contacting the aptasensor with the sample including hemin to bind the first aptamer with hemin and the second aptamer with the target material; adding a substrate for 1,1'-oxalyldiimidazole (ODI) chemiluminescence (CL), and measuring intensity of CL.

6 Claims, 6 Drawing Sheets
Specification includes a Sequence Listing.

SEQUENCE LISTING

<160> NUMBER OF SEQ ID NOS: 18

<210> SEQ ID NO 1
<211> LENGTH: 26
<212> TYPE: DNA
<213> ORGANISM: Artificial Sequence
<220> FEATURE:
<223> OTHER INFORMATION: Hermin aptamer

<400> SEQUENCE: 1
taaagggtag ggcgggttgg gtaaat                                          26

<210> SEQ ID NO 2
<211> LENGTH: 18
<212> TYPE: DNA
<213> ORGANISM: Artificial Sequence
<220> FEATURE:
<223> OTHER INFORMATION: CEA aptamer

<400> SEQUENCE: 2
ataccagctt attcaatt                                                   18

<210> SEQ ID NO 3
<211> LENGTH: 61
<212> TYPE: DNA
<213> ORGANISM: Artificial Sequence
<220> FEATURE:
<223> OTHER INFORMATION: Aptasensor including prostate specific antigen
      (PSA) aptamer as the second aptamer (PH)

<400> SEQUENCE: 3
tttttaatta aagctcgcca tcaaatagct aaaaataaag ggtagggcgg gttgggtaaa    60
t                                                                     61

<210> SEQ ID NO 4
<211> LENGTH: 80
<212> TYPE: DNA
<213> ORGANISM: Artificial Sequence
<220> FEATURE:
<223> OTHER INFORMATION: Atbasensor including Norovirus specific aptamer
      as a second aptamer (NH)

```
<400> SEQUENCE: 4
gtctgtagta gggaggatgg tccggggccc cgagacgacg ttatcaggca aaaataaagg    60
gtagggcggg ttgggtaaat                                                80

<210> SEQ ID NO 5
<211> LENGTH: 18
<212> TYPE: DNA
<213> ORGANISM: Artificial Sequence
<220> FEATURE:
<223> OTHER INFORMATION: Aptamer (CEA)

<400> SEQUENCE: 5
ataccagctt attcaatt                                                  18

<210> SEQ ID NO 6
<211> LENGTH: 30
<212> TYPE: DNA
<213> ORGANISM: Artificial Sequence
<220> FEATURE:
<223> OTHER INFORMATION: Aptamer (PSA)

<400> SEQUENCE: 6
tttttaatta aagctcgcca tcaaatagct                                     30

<210> SEQ ID NO 7
<211> LENGTH: 25
<212> TYPE: DNA
<213> ORGANISM: Artificial Sequence
<220> FEATURE:
<223> OTHER INFORMATION: aptamer (MUC1)

<400> SEQUENCE: 7
gcagttgatc ctttggatac cctgg                                          25

<210> SEQ ID NO 8
<211> LENGTH: 72
<212> TYPE: DNA
<213> ORGANISM: Artificial Sequence
<220> FEATURE:
<223> OTHER INFORMATION: Aptamer (HbA1c)

<400> SEQUENCE: 8
ggcaggaaga caaacacatc gtcgcggcct taggaggggc ggacgggggg gggcgttggt    60
ctgtggtgct gt                                                        72

<210> SEQ ID NO 9
<211> LENGTH: 30
<212> TYPE: DNA
<213> ORGANISM: Artificial Sequence
<220> FEATURE:
<223> OTHER INFORMATION: Aptamer (Insulin)

<400> SEQUENCE: 9
ggtggtgggg ggggttggta gggtgtcttc                                     30

<210> SEQ ID NO 10
<211> LENGTH: 71
<212> TYPE: DNA
<213> ORGANISM: Artificial Sequence
<220> FEATURE:
<223> OTHER INFORMATION: Aptamer (BNP)

<400> SEQUENCE: 10
tacgggagcc aacaccacct ctcacattat attgtgaata cttcgtgctg tttagagcag    60
```

```
gtgtgacgga t                                                              71

<210> SEQ ID NO 11
<211> LENGTH: 40
<212> TYPE: DNA
<213> ORGANISM: Artificial Sequence
<220> FEATURE:
<223> OTHER INFORMATION: Aptamer (myoglobin)

<400> SEQUENCE: 11
ccctcctttc cttcgacgta gatctgctgc gttgttccga                               40

<210> SEQ ID NO 12
<211> LENGTH: 36
<212> TYPE: DNA
<213> ORGANISM: Artificial Sequence
<220> FEATURE:
<223> OTHER INFORMATION: Aptamer (Ochratoxin A)

<400> SEQUENCE: 12
gatcgggtgt gggtggcgta aagggagcat cggaca                                   36

<210> SEQ ID NO 13
<211> LENGTH: 76
<212> TYPE: DNA
<213> ORGANISM: Artificial Sequence
<220> FEATURE:
<223> OTHER INFORMATION: Apmater (17beta-estradiol (E2))

<400> SEQUENCE: 13
gcttccagct tattgaatta cacgcagagg gtagcggctc tgcgcattca attgctgcgc          60
gctgaagcgc ggaagc                                                         76

<210> SEQ ID NO 14
<211> LENGTH: 40
<212> TYPE: DNA
<213> ORGANISM: Artificial Sequence
<220> FEATURE:
<223> OTHER INFORMATION: Aptamer (Vibrio parahaemolyticus)

<400> SEQUENCE: 14
tctaaaaatg ggcaaagaaa cagtgactcg ttgagatact                               40

<210> SEQ ID NO 15
<211> LENGTH: 42
<212> TYPE: DNA
<213> ORGANISM: Artificial Sequence
<220> FEATURE:
<223> OTHER INFORMATION: Aptamer (Escherichia Coli O157:H7)

<400> SEQUENCE: 15
ccggacgctt atgccttgcc atctacagag caggtgtgac gg                            42

<210> SEQ ID NO 16
<211> LENGTH: 49
<212> TYPE: DNA
<213> ORGANISM: Artificial Sequence
<220> FEATURE:
<223> OTHER INFORMATION: Aptamer (Norovirus)

<400> SEQUENCE: 16
gtctgtagta gggaggatgg tccggggccc cgagacgacg ttatcaggc                     49

<210> SEQ ID NO 17
```

```
<211> LENGTH: 48
<212> TYPE: DNA
<213> ORGANISM: Artificial Sequence
<220> FEATURE:
<223> OTHER INFORMATION: CEA aptamer linked to hemin aptamer 1

<400> SEQUENCE: 17
aaaggtaggg cgggttgggt aaataaaaaa gggggtgaag ggataccc                 48

<210> SEQ ID NO 18
<211> LENGTH: 49
<212> TYPE: DNA
<213> ORGANISM: Artificial Sequence
<220> FEATURE:
<223> OTHER INFORMATION: CEA aptamer linked to hemin aptamer 2

<400> SEQUENCE: 18
ataccagctt attcaattaa aaataaaggg tagggcgggt tgggtaaat                49
```

APTASENSOR AND METHOD OF DETECTING TARGET MATERIAL

This application is a National Stage Application of International Application No. PCT/US2016/027836, filed Apr. 15, 2016, and claims the benefit of U.S. Provisional Application No. 62/148,028, filed on Apr. 15, 2015, contents of which are incorporated herein by reference in their entirety for all purposes as if fully set forth below.

TECHNICAL FIELD

The present disclosure relates to an aptasensor including both a first aptamer capable of binding with hemin and a second aptamer capable of binding with a target material, where the first aptamer and the second aptamer are connected by a nucleotide linker, and a method of detecting a target material using the aptasensor.

BACKGROUND ART

Recently, a number of biosensors for the early diagnosis and rapid prognosis of human diseases (e.g., acute myocardial infarction, cancer, infectious diseases) have been developed. This is because various fatal human diseases can often be treated if they are diagnosed early. For example, National Cancer Institute (NCI) noticed that 5-year survival rate of breast cancer patients from 2004 to 2010 in USA was 89.2%. In addition, American Cancer Society recently reported that 5-year survival rate of breast cancer patients in stages 0 and 1 is 100%. Also, 93% of breast cancer patients in stages 2 survive for 5 years or more.

In order to early diagnose human diseases, most of biosensors have generally been developed based on the principle of immunoassay operated with specific antibodies (e.g., capture and detection antibodies) capable of rapidly binding a biomarker existing in human samples (e.g., whole blood, serum, plasma, urine). A detection antibody conjugated with a specific enzyme such as horseradish peroxidase (HRP) and alkaline phosphatase (ALP) is widely used to enhance the sensitivity of biosensor. Sandwich enzyme immunoassay with a capture antibody and a detection antibody-conjugated HRP or ALP is highly sensitive with acceptable accuracy and reproducibility. However, antibodies and enzymes obtained from the sacrifice of animals are very expensive and intractable in ambient condition.

Many research groups have developed various methods to immobilize multiple detection antibodies and enzymes on the surface of nanoparticles such as gold, platinum, and silver. Using the nanoparticles modified with detection antibody-conjugated HRP, it was possible to develop more sensitive enzyme immunoassays. However, the system of biosensor was more expensive and more complicated than conventional enzyme immunoassay.

Since 1990, various aptamers composed of DNA, RNA, or peptide have been discovered and designed with the systematic evolution of ligands by exponential enrichment (SELEX). This is because the function of cost-effective aptamers are similar to or better than that of expensive antibodies. For example, the binding rate of a specific aptamer to capture a biomarker in human sample is similar to or more rapid than that of a conventional antibody.

Using the advantages of aptamer, many biosensors were developed as a medical device because the selectivity of biosensor using DNA or RNA aptamer conjugated with fluorescence dye (e.g., fluorescein, 6-FAM) are acceptable for the early diagnosis of human diseases. In general, the biosensor devised using an aptamer is called the aptasensor. Unfortunately, the sensitivity of aptasensor using a detection aptamer-conjugated fluorescent dye was not as good as that of biosensor using a detection antibody conjugated with HRP. In order to solve the disadvantages of aptasensor, recently, various nanoparticles as well as microspheres (e.g., magnetic beads) were used to enhance the sensitivity of aptasensor. Thus, the complicated aptasensors, like enzyme immunoassays, were operated with time-consuming procedures such as multiple incubations and washings.

Figure 1:
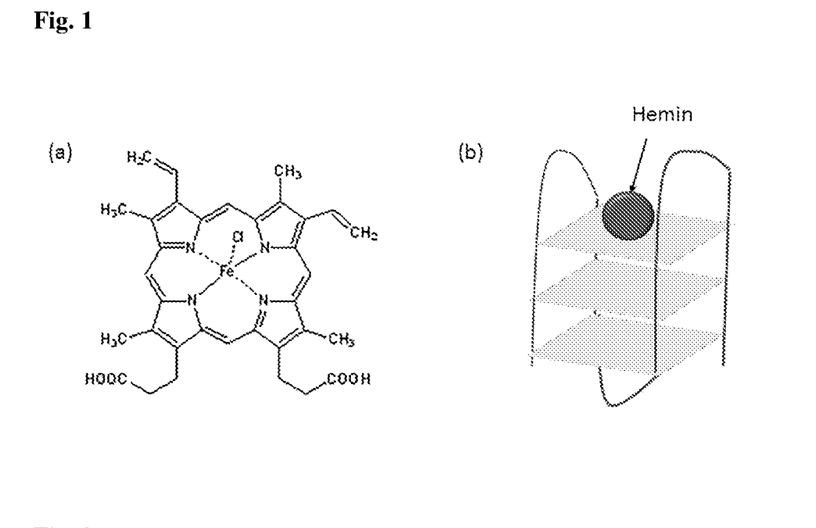
FIG. 1(a) shows chemical structure of hemin.
FIG. 1(b) shows a structure of HRP-mimicking G-quadruplex DNAzyme.

Hemin (FIG. 1(a)) is known as a HRP-mimicking compound. Also, the efficiency of hemin bound with DNA hemin aptamers, called HRP-mimicking G-quadruplex DNAzyme (FIG. 1(b)), is as good as that of HRP in enzyme immunoassay (Whillner, I., Shlyahovsky, B., Zayats, M., and Willner, B. (2008) DNAzymes for sensing, nanobiotechnology and logic gate applications, *Chem. Soc. Rev.* 37, 1153-1165). Also, the HRP-mimicking G-quadruplex DNAzyme is stable in ambient condition even though the expensive HRP must be stored in a freezer ($<-20°$ C.). Recently, several aptasensors using a mixture of aptamers and HRP-mimicking G-quadruplex DNAzyme have been developed as diagnostic methods. The aptasensor using HRP-mimicking G-quadruplex DNAzyme was more sensitive than the aptasensor using fluorescent dye. However, using a simple mixture of aptamers and HRP-mimicking G-quadruplex DNAzyme requires time-consuming procedures such as multiple incubations, as well as multiple washings after each incubation.

Colorimetric, fluorescence, and chemiluminescence are widely applied as optical detection methods of conventional immunoassays as well as aptasensors. Chemiluminescence detection is more sensitive than other optical sensors because the background of chemiluminescence emitted from a chemical reaction is lower than those of absorbance and fluorescence generated by a light source such as halogen, Xenon, and laser generated with high-voltage power supply. Luminol chemiluminescence is widely applied as a detection method of enzyme immunoassay using HRP and aptasensor using G-quadruplex DNAzyme even though 1,1'-oxalyldiimidazole (ODI) chemiluminescence is more sensitive than luminol chemiluminescence in enzyme immunoassay. ODI chemiluminescence has never been used as a detection method of aptasensor using G-quadruplex DNAzyme yet.

Carcinoembryonic antigen (CEA) is well-known as a breast cancer marker. Currently, sandwich enzyme immunoassay using a detection antibody conjugated with HRP or ALP is widely applied. Recently, two different types of DNA aptamers, capable of rapidly capturing CEA in a sample, have been developed. However, a highly sensitive aptasensor, using the CEA aptamer, has yet to be developed for the early diagnosis of breast cancer.

SUMMARY

According to one aspect, a method for detecting a target material in a sample, comprises: providing an aptasensor including a first aptamer capable of binding with hemin; a second aptamer capable of binding with the target material; and a nucleotide linker connecting the first aptamer and the second aptamer; adding hemin to the sample; contacting the aptasensor with the sample including hemin to bind the first aptamer with hemin and the second aptamer with the target material; adding a substrate for 1,1'-oxalyldiimidazole (ODI) chemiluminescence (CL); and measuring intensity of CL. The nucleotide linker may be a single strand DNA having 3-30 bases of adenine, cytosine, guanine or thymine.

The first aptamer may form HRP-mimicking G-quadruplex DNAzyme when combined with hemin. The second aptamer may be at least one selected from the group consisting of carcinoembryonic antigen (CEA) aptamer, prostate specific antigen (PSA) aptamer, and Norovirus specific aptamer. The first aptamer may be positioned in 3'-end of the aptasensor and the second aptamer may be positioned in 5'-end of the aptasensor.

In another aspect, an aptasensor comprises: a first aptamer capable of binding with hemin; a second aptamer capable of binding with a target material; and a nucleotide linker connecting the first aptamer and the second aptamer. The nucleotide linker may be a single strand DNA having 3-30 bases of adenine, cytosine, guanine or thymine. The first aptamer may form HRP-mimicking G-quadruplex DNAzyme when combined with hemin. The second aptamer may be at least one selected from the group consisting of carcinoembryonic antigen (CEA) aptamer, prostate specific antigen (PSA) aptamer, and Norovirus specific aptamer. The first aptamer may be positioned in 3'-end of the aptasensor and the second aptamer may be positioned in 5'-end of the aptasensor In yet another aspect, a kit for detecting a target material from a sample, comprises the above aptasensor and a container. The kit may further include hemin and a substrate for 1,1'-oxalyldiimidazole (ODI) chemiluminescence (CL).

These and other aspects will be appreciated by one of ordinary skill in the art upon reading and understanding the following specification.

DETAILED DESCRIPTION

According to embodiment of the present invention, a method is provided for detecting a target material in a sample by using an aptasensor having a first aptamer capable of binding with hemin; a second aptamer capable of binding with the target material; and a nucleotide linker connecting the first aptamer and the second aptamer. The method may rapidly detect and quantify a target material (e.g., biomarker) in a sample solution including hemin through 1,1'-oxalyldiimidazole (ODI) chemiluminescence (CL) detection. The target material and hemin may competitively bind with the aptasensor. When a substrate for CL detection (e.g., Amplex Red and $H_2O_2$) is added to the sample solution including hemin after the contacting with the aptasensor, the yield of resorufin formed from the reaction with the CL substrate is dependent on the concentration of HRP-mimicking G-quardruplex DNAzyme produced from the binding interaction between hemin and the aptasensor. When ODI and $H_2O_2$ are added in the sample after the contacting to produce resorufin, bright red light is emitted from the sample. The light emitted in the absence of target material is brighter than that in the presence of the target material. This is because HRP-mimicking G-quardruplex DNAzyme competitively produces a target material-bound aptasensor (dual DNA aptamer) in the second aptamer when the aptasensor and hemin are added in the sample including the target material. Thus, relative CL intensity of the aptasensor is exponentially decreased with the increase of the concentration of the target material in a sample, e.g., human serum.

The first aptamer may be a hemin aptamer which may bind with hemin to form HRP-mimicking G-quadruplex DNAzyme. The structure of HRP-mimicking G-quadruplex DNAzyme is shown in FIG. 1(b).

The aptasensor according to an embodiment of the present invention may have the following structure (Formula 1).

[Formula 1]

Hemin aptamer (SEQ IQ NO:1)
Linker
5'-XAAAAATAAAGGGTAGGGCGGGTTGGGTAAAT-3'

Aptamer capable of binding with a specific target material in a sample

In the above structure, the second aptamer (X) is linked to the first aptamer (e.g., hemin aptamer). The second aptamer (X), capable of binding with a specific target material, linked to hemin aptamer, may detect the target material in a sample. In other words, a specific target material in a sample may be quantified with X linked to hemin aptamer using the aptasensor with ODI-CL detection. The aptasensor can be used for the early diagnosis and prognosis of human diseases (e.g., cancer, cardiac aliments, diabetes, infectious diseases) and the rapid monitoring of toxic materials (biological and chemical toxins, food-borne pathogens, viruses) in a sample.

For example, the aptasensor may include CEA aptamer as the second aptamer for the early diagnosis of breast cancer as shown in Formula 2.

[Formula 2]

In addition, the aptasensor including prostate specific antigen (PSA) aptamer as the second aptamer (PH) shown in Formula 3 may be applied to sense prostate specific antigen (PSA) in human serum for the early diagnosis prostate cancer. Also, as shown in Formula 4, the aptasensor including Norovirus specific aptamer as a second aptamer (NH) may be applied to rapidly monitor Norovirus in a sample.

[Formula 3]

(SEQ ID NO: 3)
PH: 5'- TTTTTAATTAAAGCTCGCCATCAAATAGCTAAAAATAAAGGG
TAGGGCGGGTTGGGTAAAT-3'

-continued

[Formula 4]

(SEQ ID NO: 4)
NH: 5'- GTCTGTAGTAGGGAGGATGGTCCGGGGCCCCGAGACGACGTT
ATCAGGCAAAAATAAAGGGTAGGGCGGGTTGGGTAAAT-3'

In addition to the aptamers for human disease biomarkers, the second aptamer may be also aptamers for toxins, food-borne pathogens and viruses. The following TABLEs 1 and 2 shows examples of aptamers that can be used as the second aptamer.

TABLE 1

Biomarkers and aptamers for the diagnoses and prognoses of human diseases

| Biomarker | Human disease | Aptamer |
|---|---|---|
| CEA | Breast cancer | 5'-ATACCAGCTTATTCAATT-3' (SEQ ID NO: 5) |
| PSA | Prostate cancer | 5'-TTTTTAATTAAAGCTCGCCATCAAATAGCT-3' (SEQ ID NO: 6) |
| MUC1 | Breast cancer | 5'-GCAGTTGATCCTTTGGATACCCTGG-3' (SEQ ID NO: 7) |
| HbA1c | Diabetes | 5'-GGCAGGAAGACAAACACATCGTCGCGGCCTTAGGAG GGGCGGACGGGGGGGGGCGTTGGTCTGTGGTGCTGT-3' (SEQ ID NO: 8) |
| Insuline | Diabetes | 5'-GGTGGTGGGGGGGGTTGGTAGGGTGTCTTC-3' (SEQ ID NO: 9) |
| BNP | Cardiac disease | 5'-TACGGGAGCCAACACCACCTCTCACATTATATTGTG AATACTTCGTGCTGTTTAGAGCAGGTGTGACGGAT-3' (SEQ ID NO: 10) |
| Myoglobin | Carduac disease | 5'-CCCTCCTTTCCTTCGACGTAGATCTGCTGCGTTGTTC CGA-3' (SEQ ID NO: 11) |

TABLE 2

Aptamers of toxins, foodborne pathogens, and viruses

| Analyte | Type | Aptamer |
|---|---|---|
| Ochratoxin A | Biological toxin | 5'-GATCGGGTGTGGGTGGCGTAAAGGGAGCATCGGACA-3' (SEQ ID NO: 12) |
| 17β-estradiol (E2) | Chemical toxin | 5'-GCTTCCAGCTTATTGAATTACACGCAGAGGGTAGCG GCTCTGCGCATTCAATTGCTGCGCGCTGAAGCGCGGAAG C-3' (SEQ ID NO: 13) |
| Vibrio parahaemolyticus | Food-borne pathogen | 5'-TCTAAAAATGGGCAAAGAAACAGTGACTCGTTGAGA TA CT-3' (SEQ ID NO: 14) |
| Escherichia Coli O157: H7 | Food-borne pathogen | 5'-CCGGACGCTTATGCCTTGCCATCTACAGAGCAGGTGT GACGG-3' (SEQ ID NO: 15) |
| Norovirus | Virus | 5'- GTCTGTAGTAGGGAGGATGGTCCGGGGCCCCGAGA CGACGTTATCAGG C-3' (SEQ ID NO: 16) |

The nucleotide linker is a single strand DNA having 3-30 bases of adenine, cytosine, guanine or thymine. More preferably, the nucleotide linker includes 5-15 bases.

The aptasensor may have a form of single strand DNA, where the first aptamer may be positioned in 3'-end of the aptasensor and the second aptamer may be positioned in 5'-end of the aptasensor, or vice versa.

The method and system using the aptasensor may be provided in the form of a kit. In one embodiment of the present invention, the kit includes the above-described aptasensor and a container. The kit may further include hemin and substrate for 1,1'-oxalyldiimidazole (ODI) chemiluminescence (CL).

The kit may also include at least one of the following components:
1. Standards (controls) of an analyte.
2. 10-Acetyl-10H-phenoxazine-3,7-diol as a substrate capable of interacting DNAzyme.
3. 20 mM $H_2O_2$ in aqueous solution.
4. 1,1'-Oxalyldiimidazole (ODI) in organic solvent such as ethyl acetate and acetonitrile.
5. 100 mM $H_2O_2$ in organic solvent such as isopropyl alcohol and methyl alcohol.

Examples

Chemicals and Materials

Two different types of aptasensors according to one embodiment of the present invention (CEA aptamer linked to hemin aptamer; (CH-1 and CH-2)), as shown below, were prepared. CEA aptamer was linked to a hemin aptamer using a linker composed of 5 adenines (AAAAA).

CH-1:
(SEQ ID NO: 17)
5'-AAAGGTAGGGCGGGTTGGGTAAATAAAAAAGGGGGTGAAGG

GATACCC-3'

CH-2:
(SEQ ID NO: 18)
5'-ATACCAGCTTATTCAATTAAAAATAAAGGGTAGGGCGGGTT

GGGTAAAT-3'

Hemin was purchased from Sigma Aldrich. Bis (2,4,6-trichlorophenyl) oxalate (TCPO) and 4-methylimidazole (4MImH) were purchased from TCI America. 3 and 30% $H_2O_2$ were purchased from VWR. Amplex Red was purchased from Thermofisher. Deionized $H_2O$ (HPLC grade), Ethyl acetate, losropyl alcohol, and high concentration of PBS (pH 7.4, 20×) were purchased from EMD. CEA diagnostic kit for ELISA and serum diluent (0 calibrator) were purchased from Monobind, Inc. CEA antigen (25 μg) was purchased from Lee Biosolutions. 8-well EIA/RIA strip-well plate was purchased from Costar. Coded human serum samples containing various concentrations of CEA were obtained from the Washington County hospital (Alternative name: Meritus Health Service) located in Maryland, United States.

Interaction Between Hemin and the Aptasensor CH-2 (CEA Aptamer-Linker-Hemin Aptamer)

Figure 12:
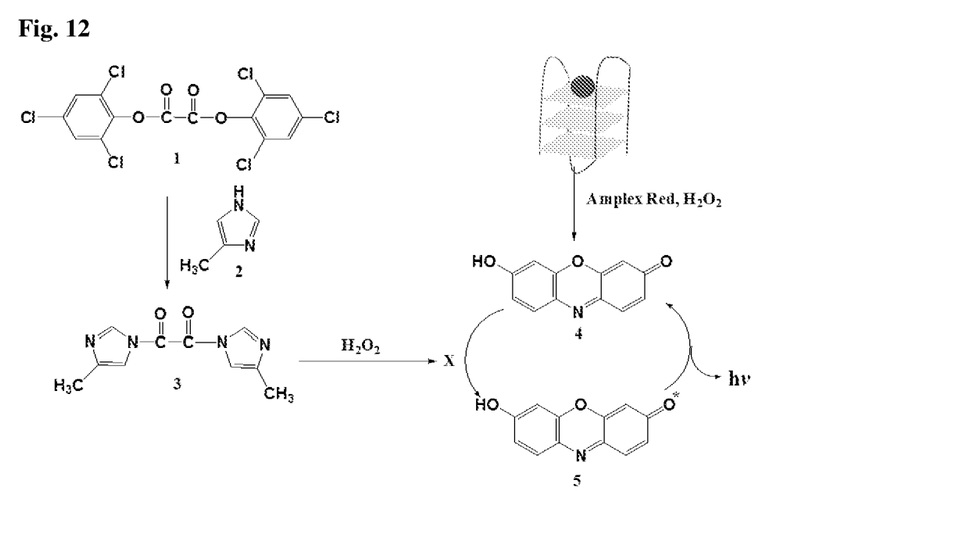
FIG. 12 depicts ODI chemiluminescence reaction in the presence of HRP-mimicking G-quadruplex DNAzyme and substrate (e.g., the mixture of Amplex Red and $H_2O_2$). 1 Bis(2,4,6-trichlorophenyl) oxalate, 2 4-methylimidazole, 3 ODI, 4 resorufin under the ground state, 5 resorufin under the excited state, X high-energy intermediate.

In order to confirm whether HRP-mimicking G-quadruplex DNAzyme is formed from the interaction between hemin and hemin aptamer in the aptasensor CH-2(CEA aptamer-linker-hemin aptamer), hemin (300 nM, 50 μl) was mixed with a certain concentration of CH-2 (50 μl) in PBS (10 mM, pH 7.4) and incubated for 20 min at room temperature. After the incubation, the mixture (100 μl) of Amplex Ultra Red (2 μM) and $H_2O_2$ (0.4 mM), a substrate for ODI chemiluminescence detection in the presence of HRP, was added in the strip-well containing hemin and CH-2. The mixture was then incubated for 6 min at room temperature. After the incubation, the mixture (10 μl) was injected into a borosilicate test tube (12 mm×75 mm). The tube was inserted into the detection area of the luminometer (Lumat LB 9507, Berthold, Inc) with two syringe pumps. 20 mM $H_2O_2$ (25 μl) dissolved in isopropyl alcohol was dispensed through the first syringe pump of the luminometer. Then, strong light immediately emitted with the addition of ODI (25 μl) using the second syringe pump was measured for 1 second. The effect of HRP-mimicking G-quadruplex DNAzyme was studied with relative CL intensity measured in the absence or presence of hemin aptamer. FIG. 12 shows the brief reaction mechanism of ODI chemiluminescence reaction in the presence of HRP-mimicking G-quadruplex DNAzyme.

Quantification of CEA in Human Serum Using the Aptasensor CH-2

In order to quantify CEA in unknown sample, 8 different standards (0, 3.13, 6.25, 12.5, 25, 50, 100, 200 ng/ml) were prepared in human serum diluent (0 calibrator). In order to produce HRP-mimicking G-quadruplex DNAzyme, each standard (40 μl) was mixed with CH-2 (250 nM, 40 μl) and hemin (740 nM, 20 μl) in a polystyrene strip-well. The mixture was incubated for 30 min at room temperature. After the incubation, the mixture of Amplex Red and H/02 was added in the polystyrene strip-well. The final mixture was incubated for 6 min to form resorufin from the reaction of substrate and HRP-mimicking G-quadruplex DNAzyme. The brightness of light (relative CL intensity) emitted in the final mixture with the addition of ODI chemiluminescence reagents (ODI and $H_2O_2$) was measured using the luminometer using the method described above. Using the linear calibration curve obtained with the relative CL intensity measured in the presence of each standard, CEA in unknown sample was quantified.

Correlation Between the Aptasensor CH-2 and Conventional ELISA

In order to study the correlation between the aptasensor CH-2 and the conventional enzyme-linked immunosorbent assay (ELISA) using HRP, 30 human serum samples containing various concentration of CEA were obtained from the Washington County Hospital. All the samples were coded to protect the information of patients. In order to determine the CEA concentration of each sample using conventional ELISA, the ELISA kits purchased from Monobind, Inc. were used. CEA concentration in each sample was determined using the aptasensor CH-2 and conventional ELISA. Then, the CEA concentration of each sample determined with the aptasensor CH-2 was compared with that measured with ELISA.

Interaction Between Hemin and the Aptasensor CH-2 (CEA Aptamer-Linker-Hemin Aptamer)

Figure 2:
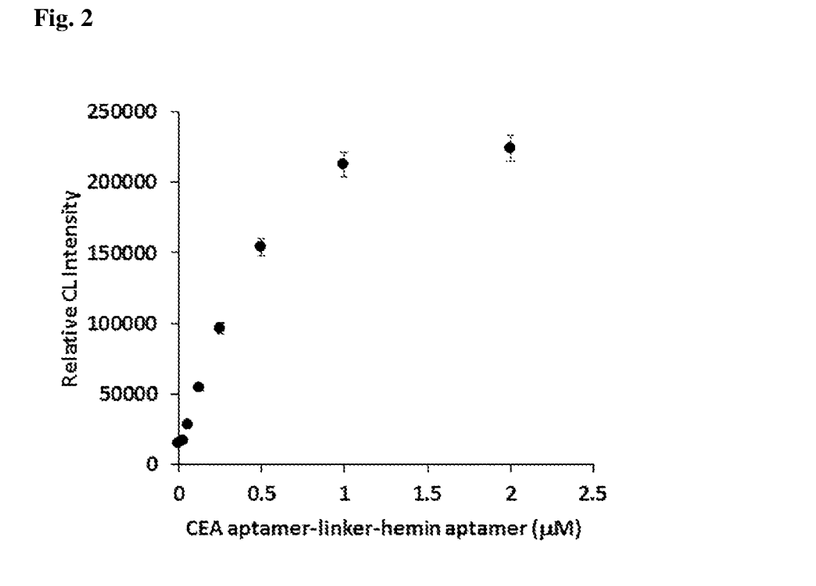
FIG. 2 is a graph showing interaction between hemin and an aptasensor according to one embodiment of the present invention (CEA aptamer-linker-hemin aptamer (CH-2)).

It is well-known that hemin rapidly binds with hemin aptamer. An experiment for checking the relative CL intensity of the aptasensor CH-2 by binding with hemin in PBS (pH 7.4) according to the concentration of the aptasensor CH-2 were conducted. As shown in FIG. 2, relative CL intensity was enhanced with the increase of CH-2 concentration. This is because HRP-mimicking G-quadruplex DNAzyme, formed from the interaction between hemin and CH-2, can strongly support the reaction of Amplex Red and $H_2O_2$ to rapidly form resorufin. The results shown in FIG. 1 indicate that it is possible to develop an aptasensor capable of quantifying CEA in human sample for the early diagnosis of breast cancer if CEA aptamer of CH-2 can rapidly bind with CEA.

Figure 3:
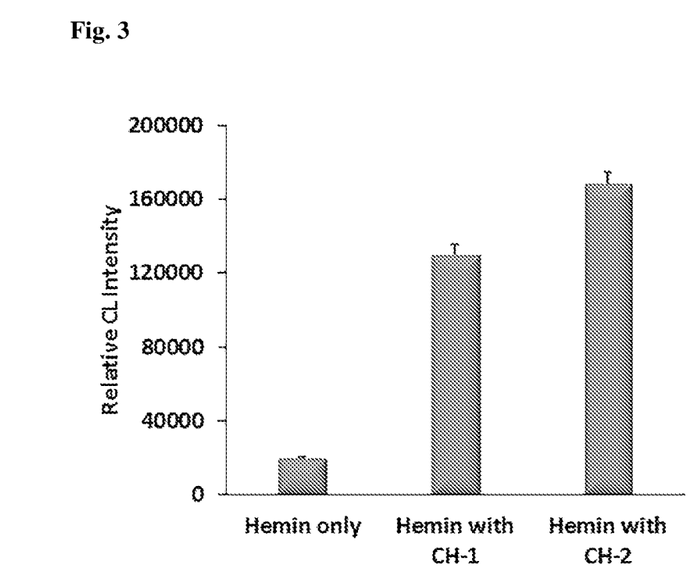
FIG. 3 is a graph showing interaction between hemine and CH-1 or CH-2 to form HRP-mimicking G-quadruplex DNAzyme.

FIG. 3 shows an interaction between hemine and CH-1 or CH-2 to form HRP-mimicking G-quadruplex DNAzyme (Condition: [CH-1] and [CH-2]=0.5 µM, [Hemin]=300 nM, Incubation time: 20 min at room temperature). FIG. 3 shows that CH-2 is better than CH-1 as a candidate to develop a highly sensitive biosensor because the interaction between hemin and CH-2 to form HRP-mimicking G-quadruplex DNAzyme is more rapid than that between hemin and CH-1.

Relative CL Intensity in the Absence and Presence of CEA

Figure 4:
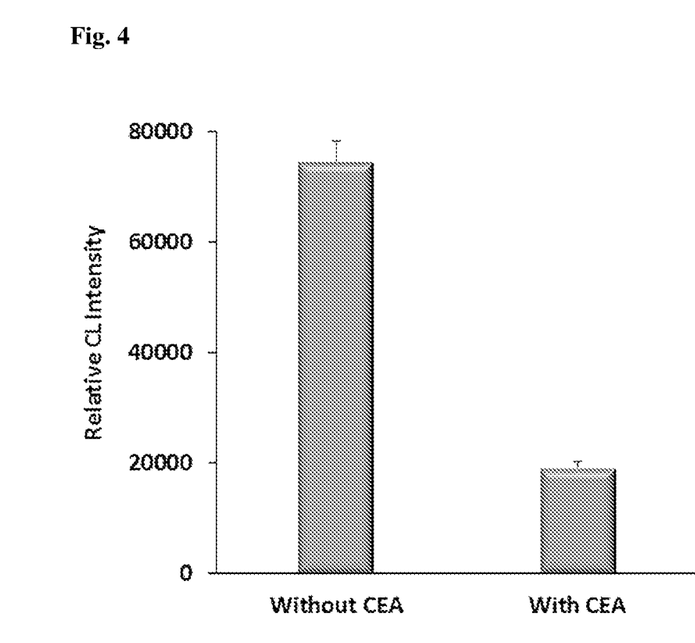
FIG. 4 is a graph showing interaction between hemin and CH-2 in the absence and presence of CEA.

As mentioned above, the aptasensor CH-2 (CEA aptamer-linker-hemin aptamer) was designed to bind with hemin as well as CEA. Thus, it was expected that the relative CL intensity in the absence of CEA could be similar to that in the presence of CEA because the brightness of ODI chemiluminescence is only dependent on the concentration of HRP-mimicking G-quadruplex DNAzyme. FIG. 4 shows an interaction between hemin and CH-2 in the absence and presence of CEA. As shown in FIG. 4, however, the relative CL intensity in the absence of CEA was about 4-fold higher than that in the presence of CEA (80 ng/ml) when hemin (740 nM) and CH-2 (1 µM) was incubated in the presence of CEA for 1 hr at room temperature. The results indicate that the hemin aptamer of free CH-2 can rapidly bind with hemin, whereas the hemin aptamer of CH-2 bound with CEA has difficulty in binding or cannot bind with hemin as shown in FIG. 5.

Figure 5:
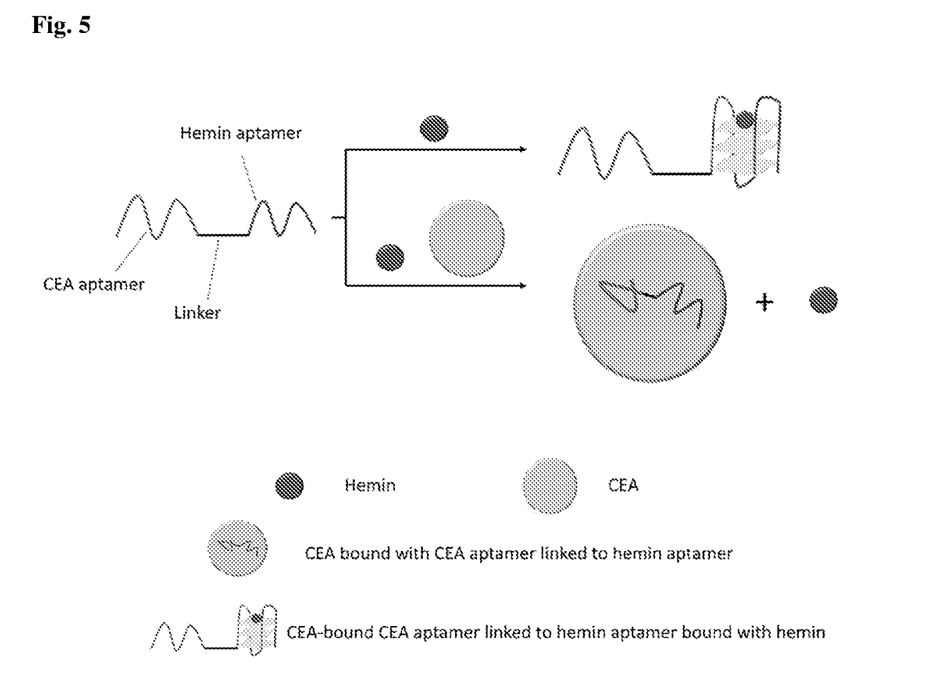
FIG. 5 depicts a possible mechanism for the interaction of CH-2 and hemin in the absence and presence of CEA.

FIG. 5 shows possible mechanism for the interaction of CH-2 and hemin in the absence and presence of CEA. As shown in FIG. 5, CEA, which is a protein, is bigger and more complicated than CH-2. Thus, it is possible that the hemin aptamer of CH-2 bound with CEA cannot bind with hemin due to the steric hindrance effect of the big and complicated CEA.

Based on the results shown in FIG. 4 and the possible mechanism as proposed above, it is possible to develop an aptasensor operated without the time-consuming washings required to generate conventional biosensors. The relative CL intensity of the aptasensor in the absence of CEA will be the highest. Then, relative CL intensity of the aptasensor will be decreased with the increase of CEA concentration in human serum. In order to optimize the function of the aptasensor, the inventor of the present invention studied more about variable factors such as the binding rate of CH-2 and CEA, incubation time and the effect of CH-2 concentration.

Indirect Determination of Binding Rate Between the Aptasensor CH-2 and CEA

Figure 6:
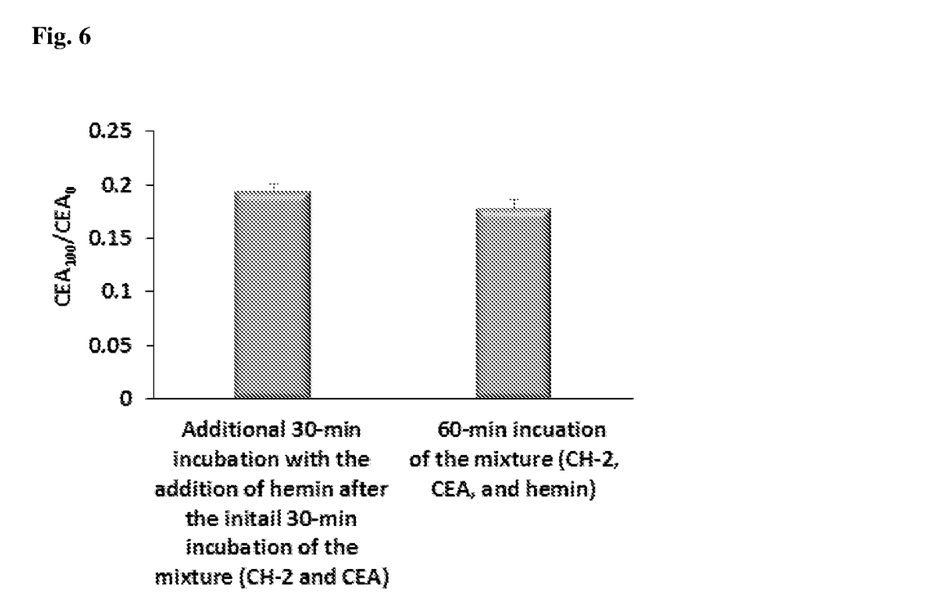
FIG. 6 is a graph showing comparison of $CEA_{100}/CEA_0$ under the two different incubation methods.

As shown in FIG. 3, it is confirmed that the hemin aptamer of CH-2 can bind with hemin within 20 min at room temperature. FIG. 6 shows comparison of $CEA_{100}/CEA_0$ under the two different incubation methods. Using the two different incubation methods shown in FIG. 6, the inventor was able to study whether the binding rate between CEA and CEA aptamer of CH-2 is as fast as that between hemin and hemin aptamer of CH-2. $CEA_0$ is the relative CL intensity measured after the incubation of the mixture (hemin and CH-2) in the absence of CEA for 60 min at room temperature. $CEA_{100}$ is the relative CL intensity measured after the incubation of the mixture (hemin, CH-2 and 100 ng/ml CEA) for 60 min at room temperature. As described in FIG. 6, however, the incubation method for measuring $CEA_{100}$ of left bar was different from that for determining $CEA_{100}$ of right bar. However, $CEA_{100}/CEA_0$ of the left bar in FIG. 6 was similar to that of the right bar. The results indicate that the CEA aptamer of CH-2 can bind with CEA within 30 min.

Determination of Incubation Time

Figure 7:
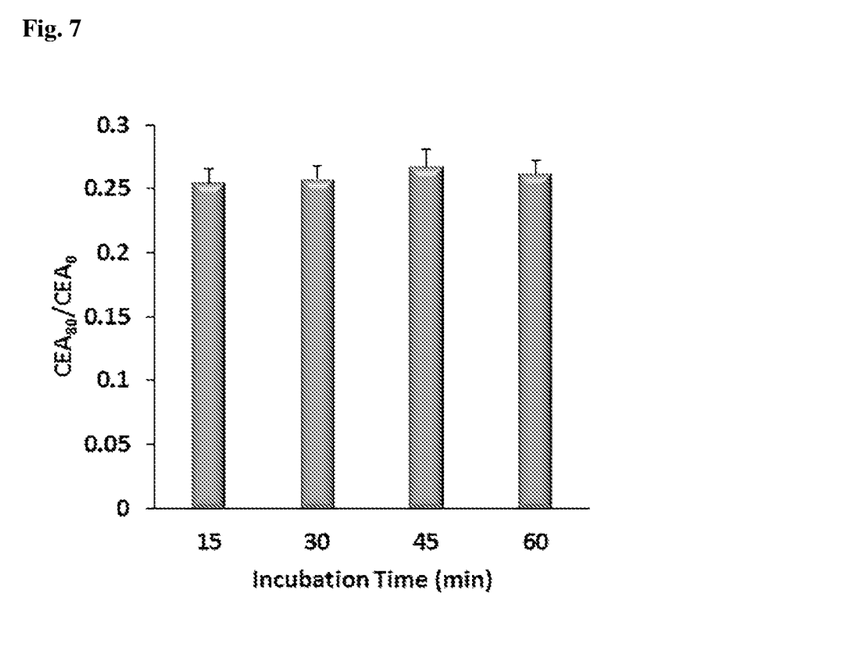
FIG. 7 is a graph showing $CEA_{80}/CEA_0$ after incubating the mixture of CEA, CH-2, and hemin for four different incubation times.

Based on the results shown in FIG. 6, CH-2 was added in the mixture of CEA and hemin at room temperature. Then, the final mixture was incubated for 15, 30, 45, and 60 min to compare $CEA_{80}/CEA_0$ computed after the four different incubations. FIG. 7 shows $CEA_{80}/CEA_0$ after incubating the mixture of CEA, CH-2, and hemin for four different incubation times. (Condition: [CEA]=80 ng/ml, [CH-2]=1 µM, [Hemin]=740 nM.) As shown in FIG. 7, the ratios of $CEA_{80}$ to $CEA_0$ ($CEA_{80}/CEA_0$) determined after the four different incubation times are the same within the statistically acceptable error range (5%). The results indicate that 15-min incubation of the mixture is enough to quantify 80 ng/ml CEA in human serum using the aptasensor CH-2. However, the concentration of CEA used is 16-fold higher than (5 ng/ml) that of cut-off value for the diagnosis of breast cancer. In other words, the 15-min incubation of the mixture may not be enough to quantify lower CEA than 5 ng/ml. Thus, 30-min incubation of mixture was selected to devise a highly sensitive and easy to use all-in-one biosensor capable of quantifying lower CEA than 5 ng/ml.

Effect of CH-2 Concentration

Figure 8:
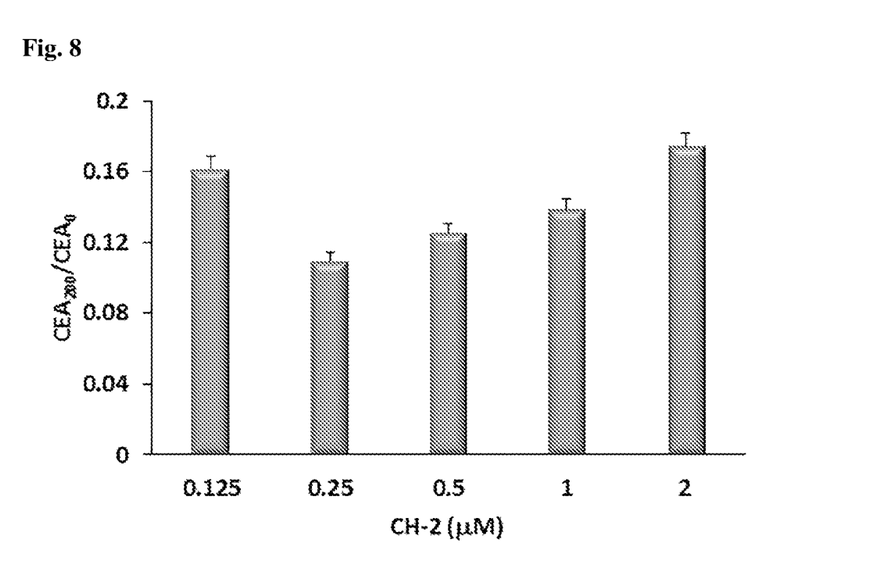
FIG. 8 is a graph showing an effect of CH-2 concentration.

FIG. 8 shows effects of CH-2 concentration. (Condition; [CEA]=200 ng/ml, [Hemin]=740 nM.) As shown in FIG. 8, $CEA_{200}/CEA_0$ was dependent on the concentration of CH-2. The best concentration of CH-2 to develop a $CEA_{100}$ biosensor was 0.25 µM. $CEA_{200}/CEA_0$ in the presence of CH-2 (0.125 µM) was larger than that in the presence of CH-2 (0.25 µM). The results indicate that the binding rate between the hemin aptamer of CH-2 and hemin is more rapid than that between CEA aptamer of CH-2 and CEA. $CEA_{200}/CEA_0$ in the presence of higher CH-2 than 0.25 µM was also larger than that in the presence of 0.25 µM CH-2. This is because the hemin molecules used to study the effect to CH-2 concentration was able to form more HRP-mimicking G-quadruplex DNAzyme in the presence of relatively excess CH-2 (>0.25 µM). Thus, $CEA_{200}/CEA_0$ was enhanced with the increase of CH-2 from 0.25 to 2 µM. Based on the experimental results, 0.25 µM CH-2 was selected to devise the aptasensor.

Quantification of CEA Using the Aptasensor

Figure 9:
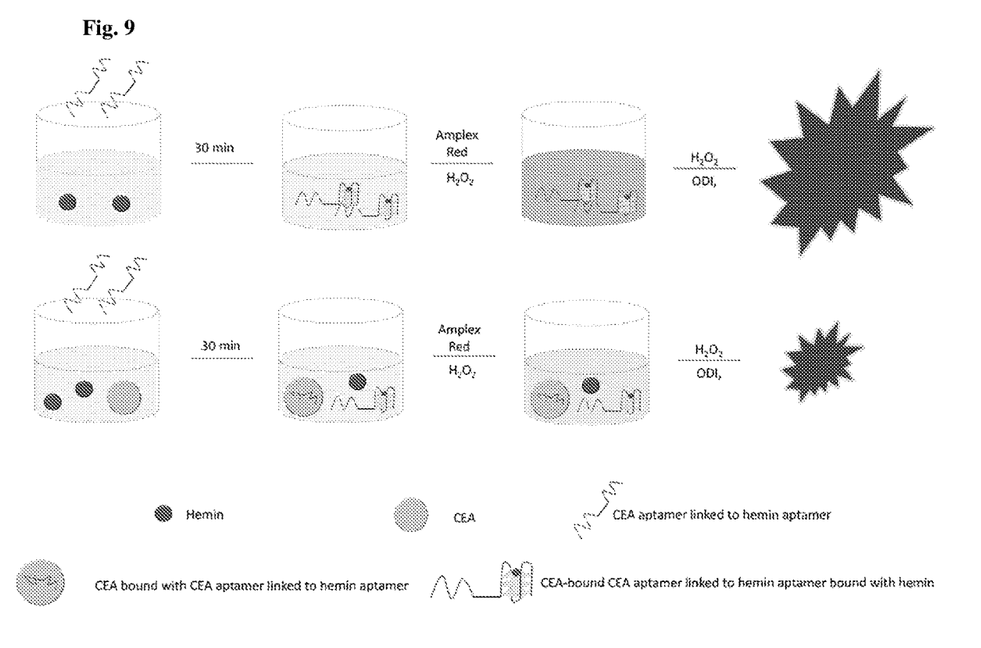
FIG. 9 depicts a method of detecting and quantifying a target material (CEA) according to one embodiment of the present invention.

The aptasensor optimized based on the preliminary experimental results described above was designed to rapidly quantify trace levels of CEA for the early diagnosis of breast cancer as shown in FIG. 9. First, the mixture containing CEA, CH-2, and hemin was incubated for 30 min at room temperature. After the incubation, Amplex Red and $H_2O_2$ were added in the mixture. Then, the final mixture was incubated for 6 min at room temperature to form resorufin. After the incubation, the strength of light immediately emitted in the mixture with addition of ODI and $H_2O_2$ was measured for 1 second. The analytical time necessary for the quantification of CEA using the aptasensor was about 2.5 times more rapid than that of commercial ELISA kit (Monibind, Inc) operated with 75 min incubation and time-consuming washings.

Figure 10:
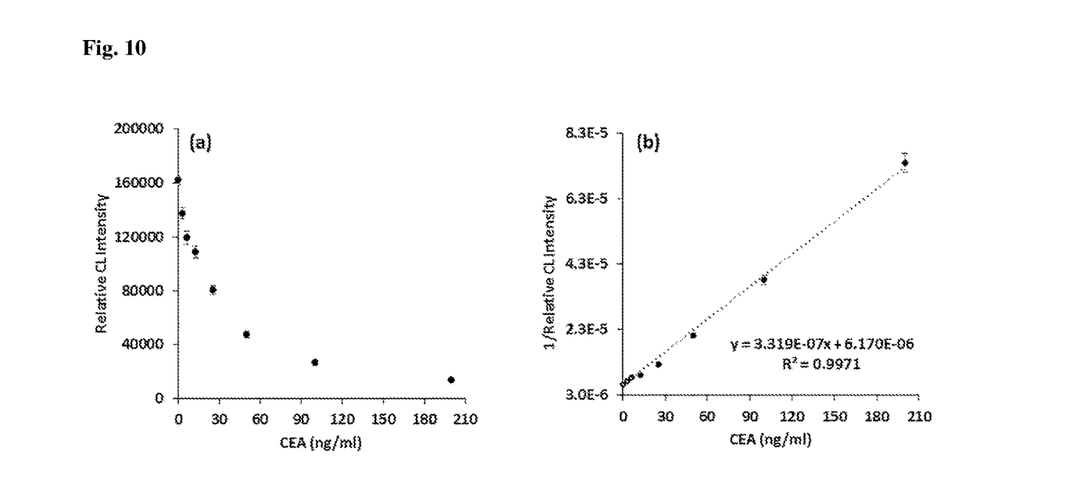
FIG. 10 is a graph showing calibration curves for the quantification of CEA.

FIG. 10 shows calibration curves of the aptasensor CH-2 using 8 different CEA standards. As shown in FIG. 10(a), the relative CL intensity exponentially decreases with the increase of CEA concentration. In order to obtain a linear calibration curve, the inverse values of relative CL intensity measured in the absence and presence of CEA was computed. As shown in FIG. 10(b), a wide linear calibration curve ($R^2$=0.9971) having a wide dynamic range (0~200 ng/ml) with good coefficient of variations (3~5%) was obtained. The limit of detection (LOD=$CEA_0$−3σ) was as low as 0.71 ng/ml. δ is the standard deviation of $CEA_0$ (N=5). LOD of all in one biosensor was lower than that (1 ng/ml) of commercial ELISA kit.

TABLE 3

Accuracy, precision, and recovery of the aptasensor CH-2 (N = 3)

| Sample 1 [a] | Sample 2 [a] | Expected [a] | Measured [a] | Recovery (%) |
|---|---|---|---|---|
| 3.0 | 5.0 | 4.0 | 4.2 ± 0.2 | 105.0 |
| 5.0 | 8.0 | 6.5 | 6.2 ± 0.3 | 95.3 |
| 8.0 | 12.0 | 10.0 | 9.7 ± 0.4 | 97.0 |
| 12.0 | 16.0 | 14.0 | 14.4 ± 0.3 | 102.9 |

[a] ng/ml
Expected = (sample 1 + sample 2)/2

As shown in TABLE 3, the aptasensor according to one embodiment of the present invention can quantify trace levels of target material (CEA) with good accuracy and precision within the statistically acceptable error range. Also, the good recovery for the mixture of sample 1 and sample 2 (1:1 volume ratio) shows the possibility that the aptasensor can be applied as a new clinical tool for the early diagnosis of human diseases (e.g., breast cancer).

Figure 11:
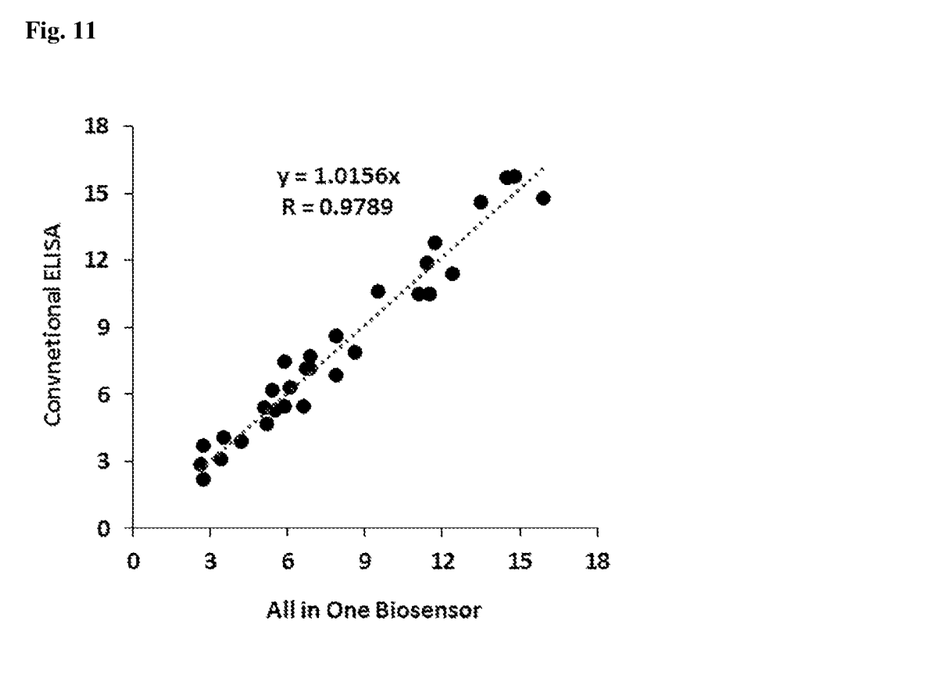
FIG. 11 is a graphs showing correlation curve between the aptasensor according to one embodiment of the present invention and a conventional ELISA.

As a method to confirm that the aptasensor can be a new diagnostic tool for the early diagnosis of human diseases (e.g., breast cancer), analytical results of 30 human serums obtained using the aptasensor CH-2 were compared with those obtained using conventional ELISA purchased from Monobind, Inc. FIG. 11 shows correlation curve between the all-in-one biosensor and conventional ELISA. As shown in FIG. 11, the correlation between the aptasensor CH-2 and conventional ELISA was good. The linear correlation curve shown in FIG. 11 indicates that the aptasensor according to the present invention is an excellent medical device capable of early diagnosing human diseases.

It is to be understood that the above-described method and aptasensor are merely illustrative embodiments of the principles of this disclosure, and that other compositions and methods for using them may be devised by one of ordinary skill in the art, without departing from the spirit and scope of the invention. It is also to be understood that the disclosure is directed to embodiments both comprising and consisting of the disclosed parts.

What is claimed is:

1. A method for detecting a target material in a sample, comprising:
   providing an aptasensor including a first aptamer capable of binding with hemin; a second aptamer capable of binding with the target material; and a nucleotide linker connecting the first aptamer and the second aptamer;
   adding hemin to the sample;
   contacting the aptasensor with the sample including hemin to bind the first aptamer with hemin and the second aptamer with the target material;
   adding a substrate for 1,1'-oxalyldiimidazole (ODI) chemiluminescence (CL); and
   measuring intensity of CL,
   wherein the second aptamer is at least one selected from the group consisting of carcinoembryonic antigen (CEA) aptamer, prostate specific antigen (PSA) aptamer, and Norovirus specific aptamer, and
   wherein the first aptamer is positioned in one end of the aptasensor and the second aptamer is positioned in the other end of the aptasensor.

2. The method of claim 1, wherein the contacting is performed less than 30 minutes at room temperature.

3. The method of claim 1, wherein the nucleotide linker is a single strand DNA having 3-30 bases of adenine, cytosine, guanine or thymine.

4. The method of claim 1, wherein the nucleotide linker is a single strand DNA having 5-15 bases of adenine, cytosine, guanine or thymine.

5. The method of claim 1, wherein the first aptamer forms HRP-mimicking G-quadruplex DNAzyme when combined with hemin.

6. The method of claim 1, wherein the first aptamer is positioned in 3'-end of the aptasensor and the second aptamer is positioned in 5'-end of the aptasensor.

* * * * *